United States Patent [19]

Cartmell et al.

[11] Patent Number: 5,106,629

[45] Date of Patent: Apr. 21, 1992

[54] TRANSPARENT HYDROGEL WOUND DRESSING

[75] Inventors: James V. Cartmell; Wayne R. Sturtevant, both of Centerville, Ohio

[73] Assignee: NDM Acquisition Corp., Minneapolis, Minn.

[21] Appl. No.: 424,559

[22] Filed: Oct. 20, 1989

[51] Int. Cl.$^5$ .............................................. A61L 15/00
[52] U.S. Cl. .................................... 424/445; 424/443; 424/447; 424/448; 424/78; 602/48; 602/57; 604/304
[58] Field of Search .............. 424/445, 443, 449, 447, 424/448; 128/156

[56] References Cited

U.S. PATENT DOCUMENTS

| | | | |
|---|---|---|---|
| 3,526,224 | 6/1967 | Potts | 128/155 |
| 3,543,750 | 1/1968 | Meizanis | 128/154 |
| 3,579,628 | 5/1971 | Gander et al. | 424/28 |
| 4,061,618 | 12/1977 | Stanley et al. | 260/29.2 |
| 4,226,232 | 10/1980 | Spence | 128/156 |
| 4,393,048 | 7/1989 | Mason, Jr. et al. | 424/132 |
| 4,460,369 | 7/1984 | Seymour | 604/897 |
| 4,517,326 | 5/1985 | Cordts et al. | 524/310 |
| 4,538,603 | 9/1985 | Pawelchak et al. | 128/156 |
| 4,595,001 | 6/1986 | Potter et al. | 128/156 |
| 4,657,006 | 4/1987 | Rawlings et al. | 128/156 |
| 4,669,458 | 6/1987 | Abraham et al. | 604/180 |
| 4,704,119 | 11/1987 | Shaw et al. | 604/897 |
| 4,743,249 | 5/1988 | Loveland | 424/447 |
| 4,747,401 | 5/1988 | Potter et al. | 128/156 |
| 4,753,232 | 6/1988 | Ward | 128/156 |
| 4,759,354 | 7/1988 | Quarfoot | 128/156 |
| 4,909,244 | 3/1990 | Quarfoot et al. | 128/156 |
| 4,921,704 | 5/1990 | Fabo | 424/446 |

FOREIGN PATENT DOCUMENTS

| | | |
|---|---|---|
| 0174803 | 3/1986 | European Pat. Off. . |
| 8801877 | 3/1988 | Int'l Pat. Institute . |
| 2198441 | 6/1988 | United Kingdom . |

OTHER PUBLICATIONS

Smith & Nephew advertisement describing a Flexigrid Application System, copyright 1990, 10,000 copies distributed.

Smith & Nephew abstract of lecture presented at Advanced Wound Care Symposium, Mar. 12, 1990.

Commonly assigned U.S. patent application Ser. No. 430,188, filed Nov. 1, 1989.

Primary Examiner—Thurman K. Page
Assistant Examiner—James M. Spear
Attorney, Agent, or Firm—Killworth Gottman Hagan & Schaeff

[57] ABSTRACT

A flexible, transparent wound dressing product contains a clear hydrogel material in a gel-like phase. The wound dressing product is comprised of several layers including a wound dressing, a release layer, and a dimensionally stable backing member. The wound dressing is comprised of a thin-film transparent layer having an adhesive perimeter portion and a center portion, and a hydrogel material positioned in the center portion of the transparent layer. Since the wound dressing is transparent, a grid pattern may be printed on the thin-film transparent layer to permit measurement of a wound. During manufacture, a vacuum pressure is applied to allow temporary access to the center portion of the thin-film transparent layer, creating a cavity for insertion of the hydrogel material. The dimensionally stable backing member is then adhesively attached around the perimeter portion of the thin-film transparent layer to help the wound dressing maintain its shape. When the wound dressing product is to be applied to a wound site, the release layer is removed, preferably using an extending tab attached thereto, to expose the hydrogen material. The remaining layers of the wound dressing product are then applied to the wound site, with the hydrogel material directly contacting the wound. Once these layers are in place, the dimensionally stable backing member is removed, preferably using an extending tab attached thereto.

17 Claims, 4 Drawing Sheets

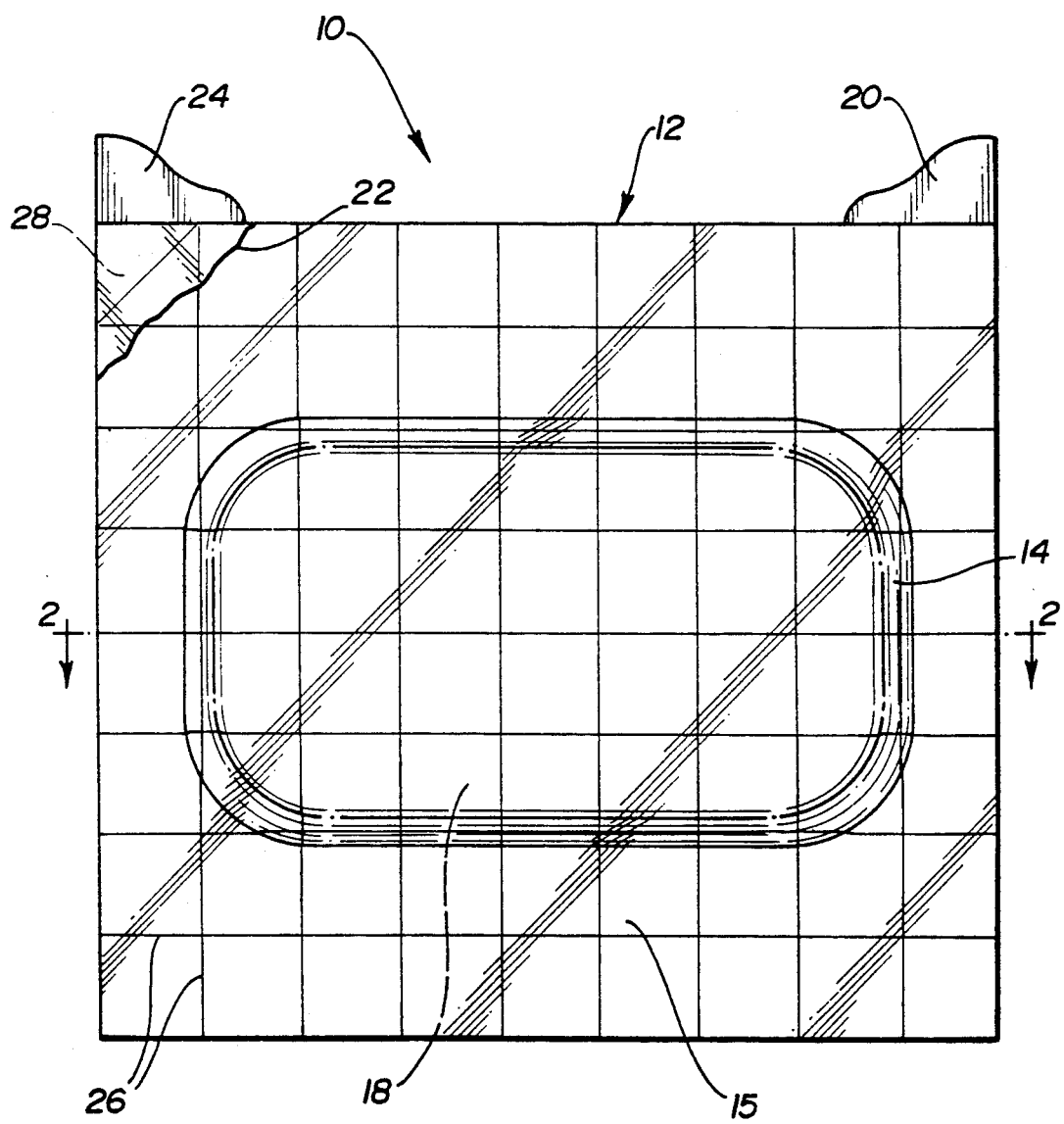

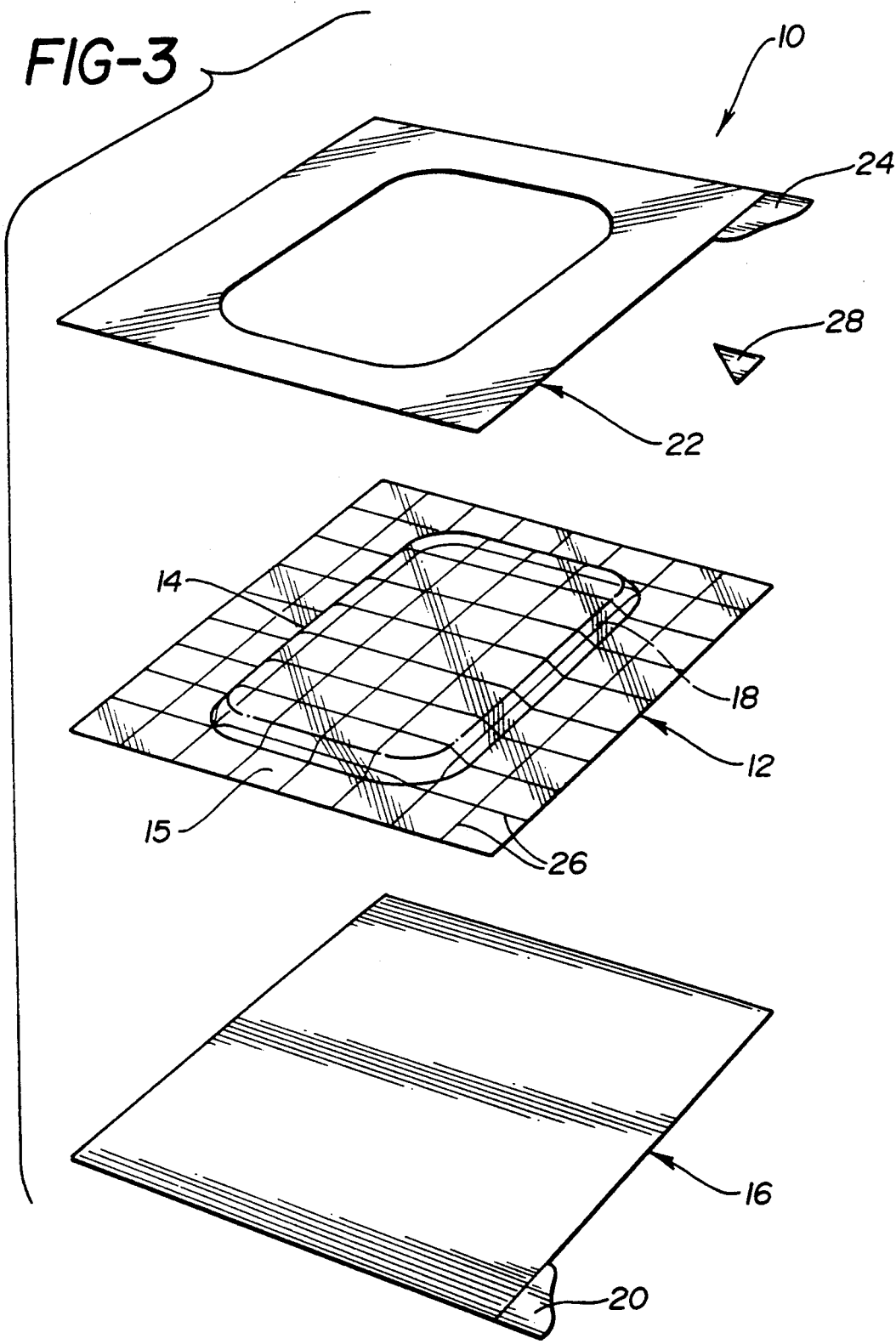

TRANSPARENT HYDROGEL WOUND DRESSING

BACKGROUND OF THE INVENTION

This invention relates to wound dressings and, more particularly, to a transparent, flexible wound dressing product containing a hydrogel substance.

Secreting skin wounds, such as decubitus ulcers and open surgical wounds, have long presented a medical challenge in keeping such wounds sterile and relatively dry. The accumulation of wound exudate, such as blood, Pustulation, and other wound fluids, in wound crevices promotes growth of bacteria and crusted organisms which cause infection and delay the healing process. However, since it is often desirable to allow a wound to heal in a slightly "moist" or occlusive state as it is believed that this may accelerate healing, excess wound exudate must be removed. If excess wound exudate remains on a wound, a "blister" of exudate can form under the wound dressing which is not only unsightly, but also may cause the dressing to leak, thereby defeating the aim of sterility. However, existing methods of aspiration can lead to wound infection or can destroy sterility. Additionally, it is not desirable to remove all the exudate as that would result in a "dry" wound and hence a slower healing process.

One existing wound exudate absorption method is to apply a hydrogel composition to a wound. As disclosed in Mason, Jr. et al, U.S. Pat. No. 4,393,048, issued July 12, 1983, a currently existing hydrogel wound treatment composition dries to a powder form after it is introduced to an open, draining wound to absorb wound exudate. However, dry hydrogel deteriorates as the wound fluids are absorbed resulting in lumping and uneven application. Additionally, such deteriorated lumps are difficult to remove from a wound site without damaging new cell tissue at the wound site. Furthermore, the progress of wound healing cannot be determined without removing, at least partially, the wound dressing from the wound site.

Aqueous moisture absorbing materials, such as a hydrogel material with a polyethylene glycol liquid curing agent as disclosed in Spence, U.S. Pat. No. 4,226,232, issued Oct. 7, 1980, are easier to remove from the wound site, but cannot be sterilized by irradiation due to the formation of free radicals within the aqueous material. Another aqueous absorbing material used to absorb wound exudate, hydrophilic polymer, is disclosed in Rawlings et al, U.S. Pat. No. 4,657,006, issued Apr. 14, 1987. In the Rawlings et al reference, a wound dressing is described which comprises a hydrophilic polymer having moisture vapor permeability characteristics. One problem with the Rawlings et al wound dressing is that the wound exudate absorbed by the hydrophilic polymer hardens the polymer, allowing pockets to develop between the polymer and the wound, providing an excellent environment for bacteria proliferation.

Known aqueous moisture absorbing wound dressing systems have additional problems, in that the aqueous material is generally contained in the center portion of a wound dressing, with a bulky adhesive border, such as a foam border. Problems with such borders include decreased comfort, conformity and adhesion as well as the existence of a "lifting edge" that can catch on clothes or bed sheets, thereby exposing the wound to bacteria and infection. In addition, observation of the wound by medical personnel may require lifting the wound dressing thereby exposing the wound, again creating a situation where bacteria and infection can be introduced to the wound site.

An existing method of overcoming the problems associated with bulky wound dressings is disclosed in Potts, U.S. Pat. No. 3,526,224 issued Sep. 1, 1970. The Potts reference discloses a wound dressing comprised of an elastomeric polyurethane film which acts as a second skin during the wound healing process. One problem with the Potts wound dressing, however, is that the "second skin" requires surgery to remove it after the wound has healed. A method which overcomes the surgical removal requirement of the Potts wound dressing is disclosed in Melzanis, U.S. Pat. No. 3,543,750, issued Dec. 1, 1970. The Melzanis reference discloses a wound dressing having a low degree of adhesion which can be easily removed from a wound site after the wound has healed. However, the low degree of adhesion impairs the ability of the Melzanis wound dressing to adhere to a wound during the healing process.

It would be desirable to provide a wound dressing product which could be precut, sterilized, and readily available for application to a draining wound. It would also be desirable to provide a wound dressing containing an exudate absorbing composition which would not decay or harden as the exudate is absorbed. In addition, it would be desirable to provide a transparent wound dressing which would permit observation of the wound without removal of the wound dressing. Further, it would be desirable to provide a wound dressing which could be removed neatly and, more importantly, without adhering to the new cell tissue of the wound. Finally, it would be desirable to provide a wound dressing with improved conformity and adhesion which could be comfortably applied to any area on a body.

SUMMARY OF THE INVENTION

The present invention meets these needs by providing a thin-film, transparent wound dressing containing an aqueous hydrogel material. The present invention also provides a method of manufacture and application of a wound dressing product which includes the wound dressing. The wound dressing product herein can be manufactured to any desirable size to provide a thin-film, fluid absorbing dressing for any size wound. The wound dressing herein is transparent, conformable and adhesive around its perimeter portion, and non-adhesive over the wound site.

The wound dressing product of the present invention comprises a release liner layer, a transparent thin-film layer containing a hydrogel material, a dimensionally stable backing member, a first adhesive layer located between the transparent layer and the release layer, and a second adhesive layer located between the transparent layer and the dimensionally stable backing member. The transparent layer containing the hydrogel material and the first adhesive layer comprise a wound dressing. The transparent, preferably polyurethane, thin-film layer, generally of a rectangular shape, has an adhesive perimeter portion and a center portion, wherein the hydrogel material covers the area of the first adhesive layer located in the center portion. In a preferred embodiment of the invention, a grid pattern is printed on the transparent film to permit wound size measurements and observation of the wound healing process without removal of the wound dressing. The grid pattern can be used to measure a wound site as the wound heals. Via the first adhesive layer, the transparent film is adhesively attached to the release liner which can have a tab extending beyond the transparent layer to facilitate removal of the release liner when the wound dressing product is to be applied to the wound.

The hydrogel material is insertable into the center portion of the transparent film, the hydrogel material having healing and absorbing qualities. The hydrogel material is preferably a saline solution in an aqueous gel-like phase, and is contained within the center portion of the transparent film. The gel-like consistency of the hydrogel material creates a bond between the wound dressing and the wound site without creating an actual adhesive attachment that would damage new cell tissue upon removal. An advantage of the gel-like hydrogel is that it will not deteriorate as the wound fluids are absorbed. Additionally, it permits clean and neat removal of the wound dressing when the wound heals or the dressing is changed.

Since the transparent film and aqueous hydrogel are extremely flexible and pliable, a dimensionally stable backing member is included in the wound dressing product to maintain the wound dressing in its desired shape until the wound dressing product is applied to a wound. The dimensionally stable backing member may define a center aperture whereby the center aperture surrounds, but does not overlie, the hydrogel material. Again, a tab extending beyond the transparent layer may be provided to facilitate removal of the dimensionally stable backing member from the wound dressing after the wound dressing product is applied to the wound.

The present invention provides a method of manufacturing the wound dressing product. Initially, the transparent film is provided, preferably of a polyurethane material, and the grid pattern may be printed on the film to allow measurement of the wound site. A first side of the transparent film is coated with the preferably medical grade first adhesive layer and a second side of the transparent film is laminated to the dimensionally stable backing member, via the second adhesive layer. The backing member, which may be any suitable material such as Flexmark 300 manufactured by Flexcon, comprises a layer of the wound dressing product to provide dimensional stability to the extremely flexible and pliable transparent layer containing the hydrogel, which otherwise has difficulty maintaining its original shape. In a preferred embodiment of this invention, the dimensionally stable backing member defines a center aperture so the backing member surrounds the perimeter portion of the transparent layer, but does not cover the hydrogel area.

The method of manufacturing the wound dressing product also includes the step of applying a vacuum pressure to the center portion of the transparent film to provide temporary access to the center portion. During the vacuum pressure, the non-adhesive hydrogel material is inserted in the center portion of the transparent film. The wound dressing comprising the transparent layer, the hydrogel material, and the first adhesive layer, is then laminated to the release liner, preferably of a silicone coated material, using the second adhesive layer.

Finally, the present invention provides a method of application of the wound dressing product described above. When the wound dressing product is to be applied to a wound site, the release liner is partially removed to expose the hydrogel material so the hydrogel can contact the wound site. A tab extending beyond the transparent layer may be provided on the release liner so removal of the release liner can be accomplished while minimizing contact between the person applying the wound dressing product and the wound dressing product itself. The wound dressing product is then applied directly over the wound in a rolling motion, while continuing to remove the release liner until the release liner is completely removed and the wound dressing completely covers the wound.

Directly contacting the wound is the hydrogel material, where it creates a bio-compatible, bacterial protective, fluid absorbing, cushioned skin-like media to facilitate the healing process. The wound dressing product is then securely attached to the healthy skin surrounding the wound site by gently pressing into place the adhesive edge, created by the first adhesive layer, of the transparent film. Once the wound dressing product has been placed on the wound site and the adhesive edge of the transparent film has been attached to the healthy skin surrounding the wound site, then the dimensionally stable backing member can be removed, preferably using a tab extending beyond the transparent layer provided with the backing member. The result is a wound dressing product including a transparent wound dressing which allows observation of the wound without removal of the dressing, the wound dressing containing a bio-compatible, non-irritating, fluid absorbing, skin-like media hydrogel material. Conformity and, more importantly, bacterial protection is improved since there is no "lifting edge" to catch on clothing or bed sheets.

It is an object of the present invention to provide a wound dressing product containing an aqueous hydrogel substance which is particularly advantageous when used to dress exuding wounds, such as decubitus ulcers, by providing a skin-like media which is bio-compatible, non-irritating, fluid absorbing, and bacterial protective; to provide a wound dressing having improved adhesive and conforming features; to provide a wound dressing which is transparent, thereby allowing medical personnel to observe the healing progression of a wound without removing the wound dressing; to provide a wound dressing which is more flexible and less bulky than existing dressings; to provide a wound dressing which will not adhere to new cell tissue when it is removed; and to provide a wound dressing product with the above features that is precut, sterilized, and readily available for application to a wound site.

Other objects and advantages of the invention will be apparent from the following description, the accompanying drawings, and the appended claims.

BRIEF DESCRIPTION OF THE DRAWINGS

FIG. 1 is a plan view of the wound dressing product;

FIG. 3 is an exploded view, illustrating the layers which form the preferred embodiment of the wound dressing product.

DETAILED DESCRIPTION OF THE INVENTION

The present invention relates to a wound dressing Product for application to a wound which includes a wound dressing comprised of a thin-film transparent layer and a hydrogel material. The invention also includes a method of manufacture and a method of application for the disclosed wound dressing product.

The wound dressing product 10 of the present invention is illustrated in FIGS. 1, 2A, 2B, and 3. Although the wound dressing product 10 is shown in FIG. 1 as having a rectangular shape, it may be any of a variety of desirable shapes. The wound dressing product 10 is composed of several layers, as illustrated by the cross-sectional view of FIG. 2A and the exploded view of FIG. 3.

Figure 2A:
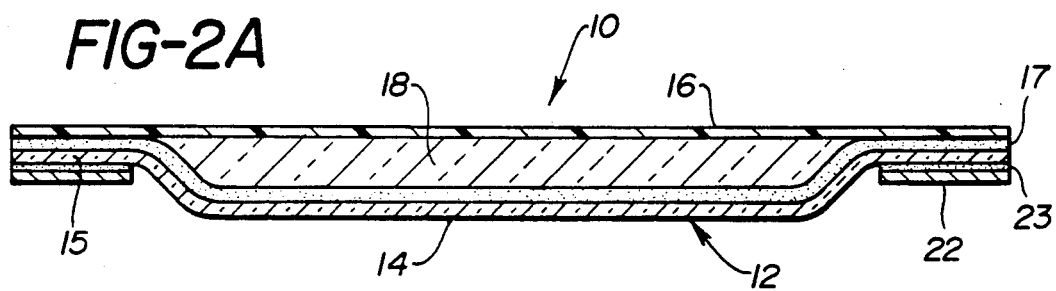
FIGS. 2A and 2B are cross-sectional views of the wound dressing product and the wound dressing, respectively, of FIG. 1 taken along line 2—2.
Figure 2B:
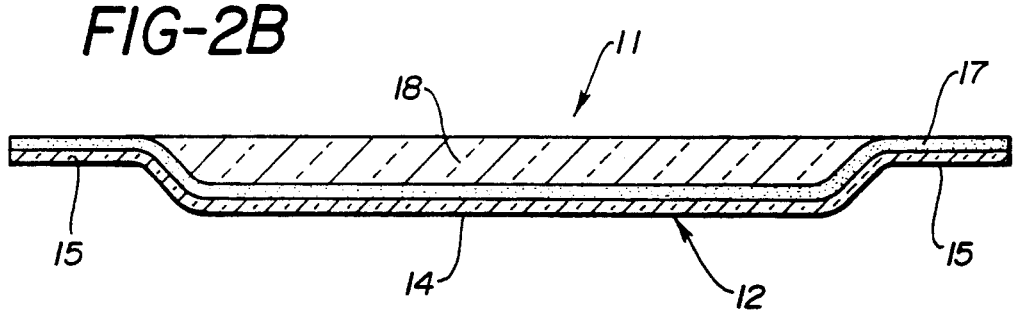

Referring now to FIG. 2A, the wound dressing product 10 is illustrated in cross-section, taken along line 2—2 of FIG. 1. The wound dressing product 10 includes a thin-film transparent layer 12, preferably of polyurethane, which has a center portion 14 and a perimeter portion 15 as illustrated in FIG. 2B. The transparent layer 12 has a first side and a second side, the first side being coated with a first adhesive layer 17. A layer of hydrogel material 18 as shown in FIGS. 1 and 2B is inserted on the first side of the transparent layer 12 in the center portion 14, thereby defining a center cavity in the center portion 14. The transparent layer 12, the first adhesive layer 17, and the hydrogel material 18 comprise a wound dressing 11, as illustrated in FIG. 2B.

The wound dressing product 10 is comprised of the wound dressing 11, a release liner layer 16, a dimensionally stable backing member 22, and a second adhesive layer 23, as illustrated in FIG. 2A. The release liner 16, preferably of a silicone-coated, sheet material, is adhesively attached to the perimeter portion 15 on the first side of the thin-film transparent layer 12 by means of the first adhesive layer 17. The release liner 16 overlies the hydrogel material 18 located in the center portion of the transparent layer 12 and the Perimeter portion 15 of the transparent layer 12. The dimensionally stable backing member 22, has a first side and a second side, the first side of which is attached to the second side of the transparent layer 12 by means of the second adhesive layer 23.

In a preferred embodiment of the present invention, as illustrated in FIGS. 1 and 3, the wound dressing product 10 includes a first tab extending from a corner of the release liner 16 and extending beyond the transparent layer 12. Additionally, a release element 28 is placed on one corner of the transparent layer 12, between the transparent layer 12 and the dimensionally stable backing member 22, as illustrated in FIG. 3. The release element 28 may be adhered along one edge to insure that it maintains its position on the transparent layer 12. A preferred embodiment of the present invention also includes a tab 24 extending from a corner of the dimensionally stable backing member 22, corresponding to the transparent layer 12 corner placement of the release element 28, and extending beyond the transparent layer 12.

In one embodiment of the present invention, a grid pattern 26 can be printed on the transparent thin-film layer 12 of the wound dressing product 10, as illustrated in FIG. 1. The grid pattern 26 allows a means for measuring the wound, observing the wound healing process, and noting the changing size of the wound site. Although FIG. 1 illustrates a rectangular grid pattern 26, any suitable grid pattern may be incorporated.

The present invention provides a method of manufacturing the wound dressing product 10. In the manufacturing method of the present invention, the release liner 16 is provided, having a first side and a second side. Additionally, the transparent layer 12 is provided, the transparent layer 12 having a first side and a second side and further having a center portion 14 and a perimeter portion 15, as illustrated in FIGS. 1 and 2B. The first side of the transparent layer 12 is coated with the first adhesive layer 17 and the first side of the dimensionally stable backing member 22 is coated with the second adhesive layer 23, which is illustrated in FIG. 2A. The second side of the transparent layer 12 is then laminated to the first side of the dimensionally stable backing member 22, wherein the second adhesive layer 23 is located between the transparent layer 12 and the dimensionally stable backing member 22, as can be seen in FIG. 2A. In a preferred embodiment of the present invention, the dimensionally stable backing member 22 and the second adhesive layer 23 define a center aperture, whereby the backing member 22 and the second adhesive layer 23 surround, but do not overlie the center portion 14 of the transparent layer 12, as illustrated in FIG. 2A.

Once the dimensionally stable backing member 22 is laminated to the second side of the transparent layer 12 and the release liner 16 is laminated to the first side of the transparent layer 12 the release liner 16 is temporarily separated from the transparent layer 12, such as by vacuum pressure to form a cavity in the center portion 14. During the vacuum pressure, a clear, gel-like aqueous material 18, preferably a hydrogel is inserted into the center portion 14 of the thin-film layer by any suitable means. The hydrogel material 18 is adhesively attached to the center portion 14 via the first adhesive layer 17 which coats the transparent layer 12. However, the first adhesive layer remains exposed around the perimeter portion 15. After the hydrogel material 18 has been inserted, the release liner 16 is reapplied to the transparent layer 12.

The hydrogel material 18 includes from about 15% to about 30% by weight of a polyhydric alcohol selected from a group consisting of polypropylene glycol, polyethylene glycol and glycerine, from about 8% to about 14% by weight isophoronediisocyanate terminated prepolymer, from about 5% to about 10% by weight polyethylene oxide based diamine, up to about 1% by weight of a salt, and the remaining percentage being water. In the preferred embodiment of the present invention, the hydrogel material 18 includes 17% propylene glycol, 12% isophoronediisocyanate terminated prepolymer, 9% polyethylene oxide based diamine, 1% salt, and 61% water. The hydrogel material 18 provides a bio-compatible, non-irritating, fluid absorbing, bacterial protective, cushioning, skin-like media over the wound site.

Figure 4A:
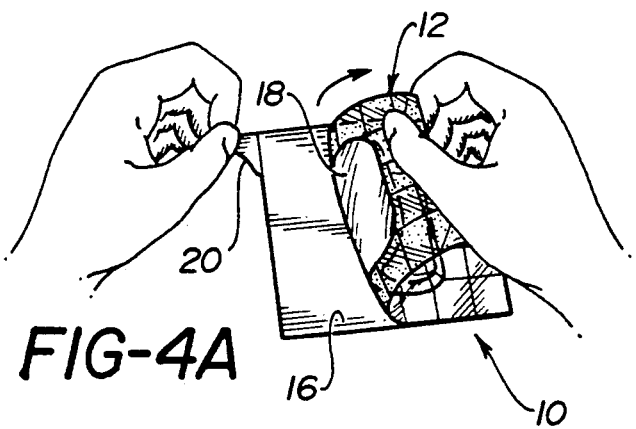
FIGS. 4A through 4D illustrate the preferred method of application of the wound dressing product of the present invention.
Figure 4B:
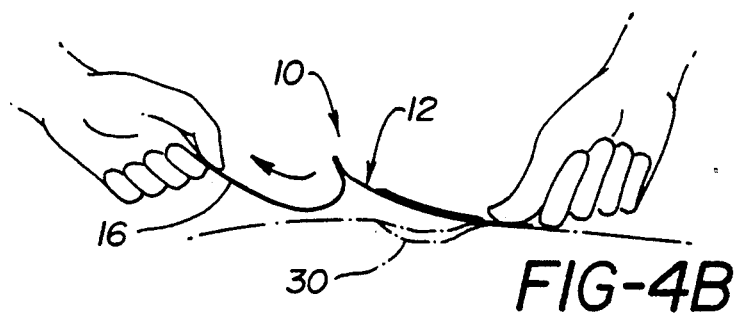
Figure 4C:
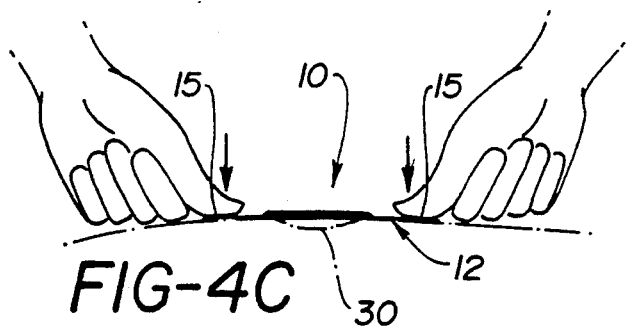
Figure 4D:
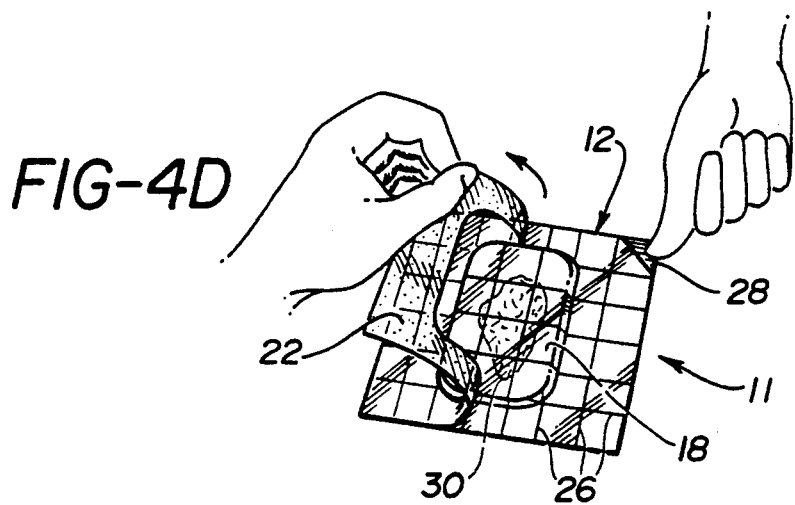

Referring now to FIGS. 4A-4D, a preferred method of application of the wound dressing product 10 is illustrated in sequence. FIG. 4A illustrates how the extending tab 20 can be gripped by the person applying the wound dressing product 10, to begin removal of the release liner 16 and expose the hydrogel material 18 before the wound dressing product 10 is applied to the wound site. In FIG. 4B, the wound dressing product 10 has been flipped over so the hydrogel material 18 can contact the wound site 30. The release liner 16 continues to be removed in a rolling motion as the transparent layer 12 is placed over the wound site 30. Once the release liner 16 has been completely removed and the remaining layers of the wound dressing product 10 are properly situated over the wound site 30, the wound dressing product 10 is secured to the wound site 30 by gently pressing into place the first adhesive layer 17 which is exposed on the perimeter portion 15, as illustrated in FIG. 4C. Finally, in FIG. 4D the dimensionally stable backing member 22, having a center aperture surrounding the hydrogel material 18, is peeled away from the transparent layer 12, to leave only the wound dressing 11 on the wound site 30.

In a preferred embodiment of the present invention, the first adhesive layer 17, located between the patient's skin and the perimeter portion 15 of the thin-film transparent layer 12, has stronger adhesive qualities than the second adhesive layer 23, located between the dimensionally stable backing member 22 and the transparent layer 12. Such a construction allows removal of the dimensionally stable backing member 22 from the wound dressing 11 while maintaining the adhesion between the perimeter portion 15 and the patient's skin. The release element 28 repels the adhesion created by the second adhesive layer 23, so as to provide a partial separation between the second adhesive layer 23 and the dimensionally stable backing member 22 sufficient to begin removal of the dimensionally stable backing member 22 from the wound dressing 11.

Once the dimensionally stable backing member 22 has been completely removed, leaving only the release element 28, the thin-film transparent layer 12, and the hydrogel material 18, the release element 28 can be lifted off the transparent layer 12 and disposed of. The result is a wound dressing 11 comprising the thin-film transparent covering 12, having an adhesive perimeter portion which adheres to the healthy skin surrounding the wound site 30 and a center portion 14 containing a wound healing hydrogel material 18.

The wound dressing product 10 of the present invention is particularly advantageous for use on exuding wounds. In particular, a special feature of the hydrogel material 18 is that it is sufficiently clear and transparent that visual observation of the wound is possible without removal of the wound dressing 11. Another benefit of the hydrogel material 18 is that it retains its gel-like integrity even upon removal of the wound dressing 11 from a wound site. The hydrogel material 18 does not leave debris in the wound when the wound dressing is removed, nor does it adhere to the wound site. The benefit of this feature is that the hydrogel material 18 exhibits a capability of non-traumatically releasing from the wound when the wound dressing 11 is removed, so as not to destroy new cell tissue forming at the wound site. Thus, healing is not inhibited by removal of the dressing 11.

Having described the invention in detail and by reference to preferred embodiments thereof, it will be apparent that modifications and variations are possible without departing from the scope of the invention which is defined in the appended claims.

What is claimed is:

1. A method of manufacturing a wound dressing product for a wound, comprising the steps of:
   providing a transparent thin-film layer, said transparent layer having a first side and a second side and further having a perimeter portion and a center portion;
   coating said first side of said transparent layer with a first adhesive layer;
   providing a removable dimensionally stable backing member defining a center aperture whereby said dimensionally stable backing member surrounds but does not overlie said hydrogel material contained in said center portion of said transparent layer, said dimensionally stable backing member having a first side and a second side;
   coating said first side of said dimensionally stable backing member with a second adhesive layer;
   laminating said second side of said transparent layer to said first side of said dimensionally stable backing member wherein said second adhesive layer is located between aid transparent layer and said dimensionally stable backing member; said first adhesive layer having stronger adhesive qualities than said second adhesive layer so as to allow removal of said dimensionally stable backing member from said transparent layer after application of the wound dressing product tot he wound while maintaining adhesion between said transparent layer and the skin of a patient;
   applying a vacuum pressure to said center portion of said transparent layer to define a cavity in said center portion;
   inserting a clear aqueous polyurethane hydrogel material in said cavity in said center portion of said transparent layer during the application of said vacuum pressure thereto;
   providing a release liner, said release liner having a first side and a second side; and
   laminating said first side of said transparent layer to said first side of said release liner wherein said first adhesive layer is located between said transparent layer and said release liner.

2. A method of manufacturing a wound dressing product as claimed in claim 1 in which the step of providing a release liner includes the step of providing a release liner having a first tab extending beyond said transparent layer to facilitate removal of said release liner when the wound dressing product is to be applied to a wound.

3. A method of manufacturing a wound dressing product as claimed in claim 1 further including the step of printing a grid pattern on said transparent layer.

4. A method of manufacturing a wound dressing product as claimed in claim 1 in which the step of providing a dimensionally stable backing member includes the step of providing a dimensionally stable backing member having a second tab extending beyond said transparent layer to facilitate removal of said dimensionally stable backing member after the wound dressing product has been applied to the wound.

5. A method of manufacturing a wound dressing product as claimed in claim 4 further including the step of Positioning a release element between said transparent layer and said backing member adjacent to said second tab, thereby further facilitating removal of said dimensionally stable backing member after the wound dressing product has been applied to the wound.

6. A method of manufacturing a wound dressing product for a wound, comprising the steps of:
   providing a transparent thin-film layer, said transparent layer having a first side and a second side and further having a perimeter portion and a center portion;

coating said first side of said transparent layer with a first adhesive layer;

providing a dimensionally stable backing member, said dimensionally stable backing member having a first side and a second side;

coating said first side of said dimensionally stable backing member with a second adhesive layer;

laminating said second side of said transparent layer to said first side of said dimensionally stable backing member wherein said second adhesive layer is located between said transparent layer and said dimensionally stable backing member; said first adhesive layer having stronger adhesive qualities than said second adhesive layer so as to allow removal of said dimensionally stable backing member from said transparent layer after application of the wound dressing product to the wound while maintaining adhesion between said transparent layer and the skin of a patient;

applying a vacuum pressure to said center portion of said transparent layer to define a cavity in said center portion;

inserting a clear hydrogel material in said cavity in said center portion of said transparent layer during the application of said vacuum pressure thereto, said hydrogel comprising:
 (a) from about 15% to about 30% by weight of a polyhydric alcohol;
 (b) from about 8% to about 14% by weight isophorone diisocyanate terminated prepolymer;
 (c) from about 5% to about 10% by weight polyethylene oxide based diamine;
 (d) up to about 1% by weight sodium chloride; and
 (e) the balance water;

providing a release liner, said release liner having a first side and a second side; and laminating said first side of said transparent layer to said first side of said release liner wherein said first adhesive layer is located between said transparent layer and said release liner.

7. A method of manufacturing a wound dressing product for a wound as recited in claim 6 wherein said hydrogel material comprises:
 (a) about 17% by weight polypropylene glycol;
 (b) about 12% by weight isophorone diisocyanate terminated prepolymer;
 (c) about 9% by weight polyethylene oxide based diamine;
 (d) about 1% by weight sodium chloride; and
 (e) about 61% water.

8. A wound dressing product for a wound, comprising:
 a wound dressing including
  a transparent layer, having a center portion and an adhesive perimeter portion surrounding said center portion, and further having a first side and a second side,
  a first adhesive layer coating, said adhesive positioned on said first side of said transparent layer, and
  a layer of an aqueous polyurethane hydrogel material positioned on said first side of said transparent layer in said center portion;
 a release liner overlying said hydrogel material and secured to said first side of said transparent layer by means of said first adhesive layer; and
 a removable dimensionally stable backing member defining a center aperture whereby said backing member surrounds but does not overlie said hydrogel material contained in said center portion of said transparent layer, said backing member having a second adhesive layer and being secured to said second side of said transparent layer, opposite said first side, by means of said second adhesive layer, wherein said first adhesive layer having stronger adhesive qualities than said second adhesive layer so as to allow removal of said dimensionally stable backing member from said transparent layer after application of the wound dressing product to the wound while maintaining adhesion between said transparent layer and the skin of a patient.

9. A wound dressing product as claimed in claim 8 wherein said release liner has a first tab extending beyond said transparent layer to facilitate removal of said release liner from said transparent layer when the wound dressing product is to be applied to a wound.

10. A wound dressing product as claimed in claim 8 wherein a grid pattern is printed on said transparent layer.

11. A wound dressing product as claimed in claim 8 wherein said dimensionally stable backing member has a second tab extending beyond said transparent layer to facilitate removal of said dimensionally stable backing member after the wound dressing product has been applied to the wound.

12. A wound dressing product as claimed in claim 11 wherein a release element is positioned between said transparent layer and said backing member adjacent to said second tab to further facilitate removal of said dimensionally stable backing member after the wound dressing Product has been applied to the wound.

13. A wound dressing product for a wound, comprising:
 a wound dressing including
  a transparent layer, having a center portion and an adhesive perimeter portion surrounding said center portion, and further having a first side and a second side,
  a first adhesive layer coating, said adhesive positioned on said first side of said transparent layer, and
  a layer of a hydrogel material positioned on said first side of said transparent layer in said center portion, said hydrogel comprising:
   (a) from about 15% to about 30% by weight polyhydric alcohol;
   (b) from about 8% to about 14% by weight isophorone diisocyanate terminated prepolymer;
   (c) from about 5% to about 10% by weight polyethylene oxide based diamine;
   (d) up to about 1% by weight sodium chloride; and
   (e) the balance water;
 a release liner overlying said hydrogel material and secured to said first side of said transparent layer by means of said first adhesive layer; and
 a dimensionally stable backing member having a second adhesive layer, said backing member secured to said second side of said transparent layer, opposite said first side, by means of said second adhesive layer, said first adhesive layer having stronger adhesive qualities than said second adhesive layer so as to allow removal of said dimensionally stable backing member from said transparent layer after application of the wound dressing product to the wound while maintaining adhesion between said transparent layer and the skin of a patient.

14. A wound dressing product as claimed in claim 8 wherein said transparent thin-film layer comprises a polyurethane material.

15. A wound dressing product as claimed in claim 8 wherein said release liner is silicone coated.

16. A wound dressing product as claimed in claim 8 wherein said first adhesive layer comprises a medical grade acrylic adhesive.

17. A wound dressing product as recited in claim 13 wherein said hydrogel material comprises:
(a) about 17% by weight polypropylene glycol;
(b) about 12% by weight isophorone diisocyanate terminated prepolymer;
(c) about 9% by weight polyethylene oxide based diamine;
(d) about 1% by weight sodium chloride; and
(e) about 61% water.

* * * * *